United States Patent
Boskamp (10) Patent No.: US 11,221,338 B2
(45) Date of Patent: Jan. 11, 2022

(54) METHOD FOR EVALUATING DATA FROM MASS SPECTROMETRY, MASS SPECTROMETRY METHOD, AND MALDI-TOF MASS SPECTROMETER

(71) Applicant: Bruker Daltonik GmbH, Bremen (DE)

(72) Inventor: Tobias Boskamp, Worpswede (DE)

( * ) Notice: Subject to any disclaimer, the term of this patent is extended or adjusted under 35 U.S.C. 154(b) by 214 days.

(21) Appl. No.: 16/342,088

(22) PCT Filed: Sep. 22, 2017

(86) PCT No.: PCT/EP2017/001131
§ 371 (c)(1),
(2) Date: Apr. 15, 2019

(87) PCT Pub. No.: WO2018/072862
PCT Pub. Date: Apr. 26, 2018

(65) Prior Publication Data
US 2019/0257839 A1    Aug. 22, 2019

(30) Foreign Application Priority Data

Oct. 17, 2016   (DE) .......................... 102016012302.8

(51) Int. Cl.
   *G01N 33/68*    (2006.01)
   *G16B 40/10*    (2019.01)
   *H01J 49/00*    (2006.01)

(52) U.S. Cl.
   CPC ......... *G01N 33/6848* (2013.01); *G16B 40/10* (2019.02); *H01J 49/0009* (2013.01); *H01J 49/0036* (2013.01)

(58) Field of Classification Search
   None
   See application file for complete search history.

(56) References Cited

U.S. PATENT DOCUMENTS

2007/0038387 A1   2/2007   Chen et al.
2012/0232805 A1   9/2012   Sadygov et al.

FOREIGN PATENT DOCUMENTS

WO   2007076606 A1   7/2007
WO   2014130627 A1   8/2014

OTHER PUBLICATIONS

Bajrami B et al., Journal of the American Society for Mass Spectrometry, vol. 20, No. 11, pp. 2124-2134, Nov. 2009.
Melinda L. Toumi et al., Journal of Proteome Research, vol. 9, No. 10, pp. 5492-5495, Oct. 2010.
Indrnil Mitra et al., Analytical Chemistry, vol. 84, No. 6, pp. 3026-3032, Mar. 7, 2012.
Haiying Zhang et al., Journal of Mass Spectrometry, vol. 44, No. 7, pp. 999-1016, Jul. 2009.
Can Bruce et al., Analytical Chemistry, vol. 78, No. 13, pp. 4374-4382, Jul. 2006.

(Continued)

*Primary Examiner* — Xiaoyun R Xu
(74) *Attorney, Agent, or Firm* — Benoit & Côté Inc.

(57) ABSTRACT

The invention relates to a method to evaluate mass spectrometry data for the analysis of peptides from biological samples, particularly MALDI-TOF mass spectrometry data, comprising the following steps:
  a) provide expected mass defects;
  b) determine measured mass defects, i.e. the mass defects resulting from the mass spectrometry data;
  c) compare the measured mass defects with the expected mass defects.

10 Claims, 10 Drawing Sheets

(56) References Cited

OTHER PUBLICATIONS

Assaf Wool et al., "Precalibration of matrix-assisted laser desorption/ionization-time of flight spectra for peptide mass fingerprinting", Proteomics, pp. 1365-1373, Nov. 2002.

Del Prete Eugenio et al., "Comparative Analysis of MALDI-TOF Mass Spectrometric Data in Proteomics: A Case Study", Network and Parallel Computing; Notes in Computer Science; Lecture Notes, Springer International Publishing, pp. 154-161, Jul. 2016.

METHOD FOR EVALUATING DATA FROM MASS SPECTROMETRY, MASS SPECTROMETRY METHOD, AND MALDI-TOF MASS SPECTROMETER

The invention relates to a method to evaluate mass spectrometry data for the analysis of peptides from biological samples, in particular MALDI-TOF mass spectrometry data. In addition, the invention relates to a mass spectrometric method for the analysis of peptides from biological samples, in particular by using a MALDI-TOF mass spectrometer. Finally, the invention relates to a mass spectrometric method for the analysis of peptides from biological samples as well as a MALDI-TOF mass spectrometer.

In so-called Matrix Assisted Laser Desorption/Ionization Time-of-Flight Mass Spectrometry (MALDI-TOF MS), a biological tissue sample is coated with a matrix solution after suitable sample preparation and is subjected to laser bombardment in a vacuum. Biological macromolecules are thereby extracted from the tissue and ionized, typically with a single positive charge. The ions are subsequently accelerated in an electric field and recorded by a detector. The m/z value, i.e. the mass-to-charge ratio of the molecule, can be determined from the time of flight. The mass spectrum measured represents the relative number of recorded ions (spectral intensity) as a function of their m/z values. Assuming a single positive ionization, the m/z value is equivalent to the mass m of the ionized molecule. In the following, for the sake of simplicity, the mass m of the ionized molecule is taken to mean the m/z value.

The m/z value or molecular mass is given in daltons (Da) as a multiple of the atomic mass unit (1 Da=1 amu). By way of approximation, the mass of a molecule in Da corresponds to the total number of protons and neutrons comprising the atomic nuclei of the molecule. The difference between this integer nominal mass and the actual mass is called the mass defect. The mass defect of a molecule is the sum of the mass defects of the individual atoms, which are in turn different for each chemical element or isotope.

The expression "mass defect" is not used uniformly in the literature. A first meaning of the term relates to the difference of the masses in the SI unit kg. A second meaning likewise relates to the difference in the masses, but is based on the atomic mass unit u, which is defined with reference to the carbon isotope 12C. This specification means the mass defect of the carbon isotope 12C is zero. The term "mass excess" is also used for this second meaning instead of the term "mass defect" to emphasize the difference to the first aforementioned meaning. In biology and chemistry, particularly in relation to mass spectrometric methods, the term "mass defect" is used nevertheless, i.e. in the sense of the second meaning; this is done here also.

In the acquisition of MALDI-TOF mass spectrometry data from biological tissue sections, a large amount of information on the proteomic structure of the tissue samples is obtained. At the same time, the measurement is subject to a number of possible interferences, which can lead to distortions and to errors in the information gained. The high level of complexity of the data means that an objective assessment of their quality and accuracy is often not possible. There are currently no widely accepted and easily applicable benchmarks which allow a statement to be made about the data quality of a measurement or whether two measurements provide data of comparable quality.

A mass spectrometric method for the analysis of peptides is known from US 2016/0003842 A1. The objective of that method is the identification of so-called glycopeptides. Mass defects are plotted against nominal masses m/z in FIGS. 2a, 2b of US 2016/0003842 A1. A distinction is made between ranges with peptides, on the one hand, and those enriched with glycopeptides, on the other hand.

A frequently occurring distortion of the measured data consists in a systematic error in the measured masses, which exceeds the tolerance limit of the measuring technology, even under carefully controlled experimental conditions. In many cases, conventional methods to correct these mass distortions are either too imprecise or too time-consuming.

The objective of this invention is to create a method for quality control of mass spectrometry data (when analyzing peptides from biological samples) or a mass spectrometric method with a corresponding control or a mass spectrometric method with a signal correction.

A method to evaluate mass spectrometric data for the analysis of peptides from biological samples is accordingly provided, in particular data from MALDI-TOF mass spectrometry, comprising the following steps:

a) provide expected mass defects;
b) determine measured mass defects, i.e. the mass defects resulting from the mass spectrometry data;
c) compare the measured mass defects with the expected mass defects.

Depending on the magnitude of the deviation of the measured mass defects from the expected mass defects, the data or a measurement on which they are based can be assessed as defective or acceptable. A corresponding signal for assessment of the data can also be output by a suitable signal source, for example a display on a screen.

If the data or the measurement are/is assessed as being acceptable, the data are processed further and/or further measurements are undertaken. When data are assessed as being defective, they can be rejected for further processing, for example, and/or the device used to carry out the mass spectrometry is checked.

The method is based on computer-aided visualization of the mass defects of the peaks found in a mass spectrum, among other things. It exploits the fact that a great many of the peaks originate from peptides whose mass defects follow a characteristic pattern. By comparing the measured mass defects with the expected mass defects/a theoretically expected mass defect pattern, conclusions can be drawn by calculatory and visual means about the quality of the measured data.

The mass spectrometric method does not measure the mass defects directly, of course. Rather, they are calculated from the masses ascertained (which are determined in a TOF mass spectrometer from measured times of flight). For simplicity, however, the term "measured mass defect" is used to distinguish it from the "expected mass defect". The latter is obtained from calculations on the basis of the special characteristics of the peptides.

A further development of the invention provides for the expected mass defects to be calculated from $$m_N \cdot r_p,$$

where $m_N$ designates the nominal mass of a peptide and $r_p$ is preferably between $10^{-3}$ and $10^{-4}$, particularly around $4.95 \times 10^{-4}$.

For the calculation of the expected mass defects, the difference to the mass m resulting from the product with $1+r_p$ is taken into account for a given (integer) nominal mass $m_N$. $r_p$ is preferably the factor $4.95 \times 10^{-4}$. Values which differ from this are also possible in principle.

A further idea of the invention provides for the mass defect for a measured mass m to be calculated from $$m - \text{floor}\left(\frac{m}{1+r_P} + 0.5\right),$$

where the function floor(x) for an arbitrary x>0 designates the integer part of x.

The measured mass defect is therefore determined as the difference between m and the nominal mass $m_N$ whose corresponding expected peptide mass $m_P=(1+r_P)m_N$ is closest to m.

A further development of the invention provides for the discrepancy $\delta_P$ between the measured and the expected mass defect to be calculated directly from the measured mass m as $$\delta_P(m) = \varphi\left(\frac{m}{1+r_P} + 0.5\right) - 0.5$$

where the function $\varphi(x)=x-\text{floor}(x)$ designates the decimal places of x for any x>0.

A further idea of the invention provides for the median of the measured mass defects to be formed and compared with the expected mass defect in order to compare the measured mass defects with the expected mass defects over subintervals of a mass axis.

In a further development of the invention, the measurements (of the masses determined) are corrected when the data are used further, i.e. depending on the deviation of the measured mass defects from the expected mass defects. In the simplest case, the masses determined are corrected by the differences of the mass defects.

According to a further idea of the invention, the measured mass defects are calculated for local maxima of the spectral intensities. Each local maximum is taken to be the peak of a specific measured mass.

The invnetion further provides for a method to evaluate mass spectrometry data for the analysis of peptides from biological samples, in particular MALDI-TOF mass spectrometry data, preferably according to one of the aforementioned methods, comprising the following steps:

a) provide expected mass defects;
b) determine measured mass defects, i.e. the mass defects resulting from the mass spectrometry data;
c) determine the discrepancies between the measured mass defects and the expected mass defects;
d) determine the variance of the discrepancies about their mean;
e) compare the variance with a defined acceptable variance.

Depending on the deviation of the variance from the defined acceptable variance, the data, or a measurement on which they are based, can be assessed as being defective or acceptable. A corresponding signal for assessment of the data can also be output by a suitable signal source, for example a display on a screen.

If the data or the measurement are/is assessed as being acceptable, the data are processed further and/or further measurements are undertaken. When data are assessed as being defective, they can be rejected for further processing, for example, and/or the device used to carry out the mass spectrometry is checked.

A further development of the invention provides for interquartile ranges of the ascertained discrepancies to be determined over subintervals of the mass axis in order to determine a variance of the mass defect discrepancies, and for the data to be rejected as defective particularly when a limit value of the variance is exceeded.

According to a further idea of the invention, an interval for acceptable variances is formed by the limit values $$d_P^{1,2}(m) = \pm\mu\sqrt{v(m)}$$

$$\text{where } v(m) = \sigma_P^2(m) + \frac{\Delta m(m)^2}{12},$$

and $\sigma_P(m_N)=\sigma_0+s_P\,m_N$, with $\sigma_0\approx 0.02$ and $s_P\approx 2.0\times 10^{-5}$,
and $\Delta m(m)$ designates the width of the m/z bins at the mass position m,
and m/z bins represent the intervals resulting from the discretization of the mass axis,
and $\mu>0$ provides a scaling factor, preferably $\mu=2$,
and where, in particular, the data are rejected as defective when the variance of the mass defect discrepancies is outside the interval thus specified.

A further development of the invention provides for the mass range with a recognizable peptide signal to be determined as the totality of all subintervals of the mass axis for which the quotient of the actual variance and the maximum permissible variance $d_P(m)$ does not exceed a specified threshold value t, where preferably t=1.2 is specified. The upper or lower limit of this mass range gives the extent of the peptide signal range.

The data, or a measurement on which they are based, can be assessed as being defective or acceptable, depending on whether a tolerance value for the upper limit is not reached, or the extent of the peptide signal range, or whether a tolerance value for the lower limit of the peptide signal range is exceeded. A corresponding signal for assessment of the data can also be output by a suitable signal source, for example a display on a screen.

If the data or the measurement are/is assessed as being acceptable, the data are processed further and/or further measurements are undertaken. When data are assessed as being defective, they can be rejected for further processing, for example, and/or the device used to carry out the mass spectrometry is checked.

To analyze peptides from biological samples, particularly by means of a MALDI-TOF mass spectrometer, the following steps are provided:

a) carry out one or more mass spectrometric analyses on the biological sample and provide data which result from the mass spectrometric analyses;
b) carry out one of the methods to evaluate data which has been presented above.

A further way of achieving the objective stated in the introduction involves a method with the following steps:

a) measure m/z values for different peptides using a measuring device, particularly by using a MALDI-TOF mass spectrometer,
b) assign the measured m/z values to corresponding m/z bins of a 2D histogram,
c) plot spectral intensities of the m/z bins in the 2D histogram, where the m/z bins are plotted on an abscissa axis and the discrepancy between measured and expected mass defect is plotted on an ordinate axis,
d) where the diagram area defined by the two axes is subdivided into a plurality, preferably 20 to 50, of rectangles,
e) where the measured values are interpolated to an m/z resolution which corresponds to the selected subdivision of the ordinate axis, and f) where, for each rectangle, those intensity values of the interpolated spectrum whose mass defect discrepancy falls within the respective subintervals of the axes are summed, g) where different intensity values are labeled differently and intensities with the same values are labeled the same.

The invention can preferably provide that, for each subinterval of the abscissa axis, in particular the horizontal mass axis, the corresponding intensity values of the ordinate axis are statistically evaluated in order to determine cluster points and/or variance values.

A further example embodiment can provide for circular statistics to be used to describe the distribution of the summed intensity values in the vertical direction, in particular a first circular moment Z can be used as the (complex-valued) statistics.

In particular, it is conceivable that the steps to form the histogram and the calculation of the circular moments are combined in order to determine a mass shift profile (vector of all circular moments Z for all subintervals of the abscissa axis, particularly the horizontal mass axis) and are expressed according to the equation $$Z_k = \frac{1}{\int_{I_k} \tilde{S}(t)dt} \int_{I_k} \tilde{S}(t)e^{i\omega t}dt, \text{ mit } \omega = \frac{2\pi}{1+r_P}$$

as Fourier integrals of the continuously interpolated spectrum $\tilde{S}$ over the subintervals $l_k$ of the abscissa axis.

A further way of achieving the objective stated in the introduction involves a mass spectrometric method provided to handle an individual spectrum, wherein for a mass shift normalization for an ensemble, for each spectrum a) a mass shift profile is determined, b) a common average reference profile is formed from all the individual mass shift profiles by forming the arithmetic mean, element by element, c) each spectrum is modified so that the mass shift profile of the modified spectrum corresponds to the reference profile.

To normalize each individual spectrum to the reference profile, there can furthermore be provision for relative shift values to be determined and interpolated over the complete mass axis for each of the individual subintervals for which the mass shift profiles are calculated, and the measured values of the spectrum are corrected by these interpolated shift values.

A MALDI-TOF mass spectrometer to achieve the aforementioned objective is herein. Accordingly, this mass spectrometer has a control unit to carry out the method according to the invention.

Further features of the invention result from the rest of the description and the Claims. Advantageous example embodiments of the invention are explained below in more detail with the aid of drawings. They show:

The molecules recorded in a MALDI measurement comprise metabolites and peptides in particular. Metabolites are metabolic products and can have various chemical forms, e.g. lipids, carbohydrates or breakdown products from substances taken up from food or the environment. Their masses are typically less than 1,000 Da. Peptides, in contrast, are chains of amino acids with masses of up to 5,000 Da and more.

All 23 amino acids which occur in proteins—and thus all peptides—consist of the five chemical elements carbon, hydrogen, oxygen, nitrogen and sulfur. For all peptides, the relative proportion of these elements is approximately the same, irrespective of their total mass, so the mass defect of a peptide is essentially determined by its nominal mass. The result is an almost linear relationship between the mass m of a peptide and its nominal mass $m_N$:

$$m \approx m_P(m_N) = (1+r_P)m_N, \text{ where } r_P \approx 4.95 \times 10^{-4}.$$

The variance of the true masses around the theoretical average $m_P$ is relatively small; its standard deviation can be estimated using $$\sigma_P(m_N) = \sigma_0 + s_P m_N, \text{ where } \sigma_0 \approx 0.02, s_P \approx 2.0 \times 10^{-5}.$$

Figure 1:
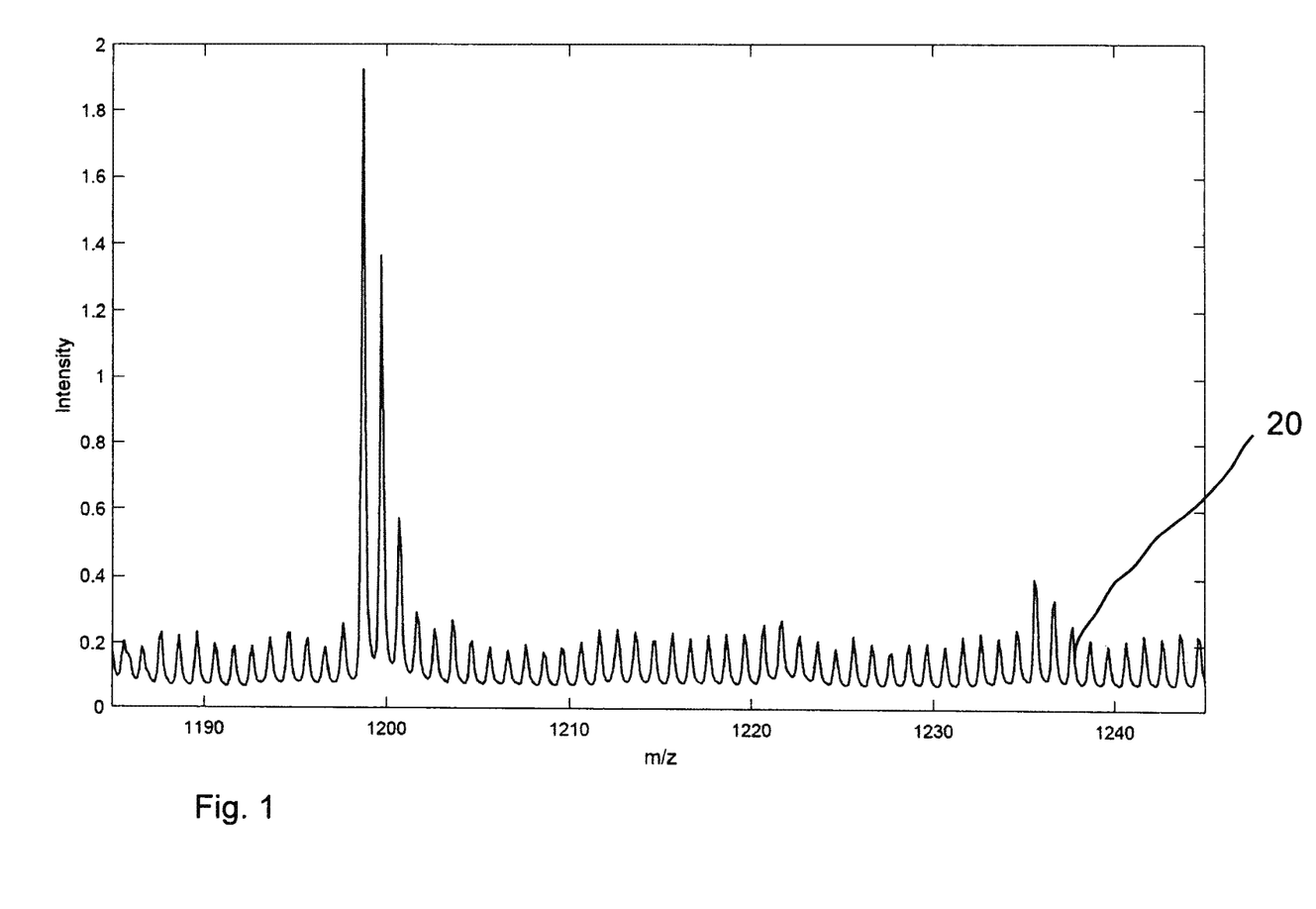
FIG. 1 a section from an average spectrum with clearly visible, wavy base line with a characteristic wavelength of slightly more than 1 Da.

The large number of different proteins and the peptides resulting therefrom in biological tissue cells means a typical MALDI spectrum has signal intensities at practically all $m_P(m_N)$ for a broad range of nominal masses $m_N$. When a sum or average spectrum is formed from several spectra obtained during the measurement of a tissue sample, see FIG. 1, a characteristic, uniform wavy line can be seen as base line 20, which stands out clearly above approx. 1,000 Da in particular, and has a wavelength of approximately $1+r_P$ Da.

The determination of the mass of a molecule is subject to an error which originates mainly from two causes: on the one hand, the time of flight of a molecule can only be measured with a certain accuracy and in discrete intervals, which results in a discretization of the mass axis, i.e. a subdivision into successive intervals (m/z bins). The width of the m/z bins is usually not constant, but increases toward higher masses.

On the other hand, the time of flight of the molecule depends not only on its mass, but also on its original state within the ion cloud at the start of the acceleration. This original state, in particular speed and direction of motion of the molecule, are largely unknown and lead to a significant measurement error, which is usually corrected by a calibration after the measurement.

The commonly used calibration methods include external calibration and statistical peptide calibration. External calibration involves placing several drops of a solution with defined constituents next to the tissue sample before the measurement. The spectra measured therein are compared with the expected masses of the known constituents after the measurement and a calibration curve is determined for the m/z axis of a spectrum. For peptide calibration, the aforementioned relationship between the true mass of a peptide and its nominal mass is utilized to shift the peak positions which are presumed to belong to a peptide to the theoretically expected m/z values, see Wool A, Smilansky Z: Precalibration of matrix-assisted laser desorption/ionization-time of flight spectra for peptide mass fingerprinting. Proteomics 2002, 2, 1365-1373.

Neither calibration method can completely correct the errors in the m/z values. External calibration, moreover, requires a manual interaction, while peptide calibration requires a large amount of computation and is time-consuming.

Since with this method, compensation of the mass errors is done globally for all spectra of a measurement, differing errors in the spectra of a data set cannot be corrected in this way. As an alternative, an internal calibration is therefore used also, wherein the calibration solution is distributed over the tissue sample being analyzed, thus enabling an individual correction for each spectrum of the measurement.

For practical reasons, a calibration solution can only contain a small number of known substances. This limits the number of reference points from which the calibration curve is determined, and thus the accuracy of the calibration. This form of calibration moreover requires a manual user interaction.

In contrast, methods of statistical peptide calibration (see Wool A, Smilansky Z: Precalibration of matrix-assisted laser desorption/ionization-time of flight spectra for peptide mass fingerprinting. Proteomics 2002, 2, 1365-1373; Wolski W E, Lalowski M, Jungblut P, and Reinert K. Calibration of mass spectrometric peptide mass fingerprint data without specific external or internal calibrants. BMC bioinformatics, 6(1): 203, 2005) are fully automatic and do not need a calibration solution. With these methods, the correction is performed by comparing the masses measured in the tissue with a theoretical peptide mass model (see above) and a peptide database. These methods require a prior peak picking, i.e. an identification of relevant peaks in a spectrum, are very time-consuming, and can lead to defective results due to an incorrect assignment between peak and peptide database.

Figure 2:
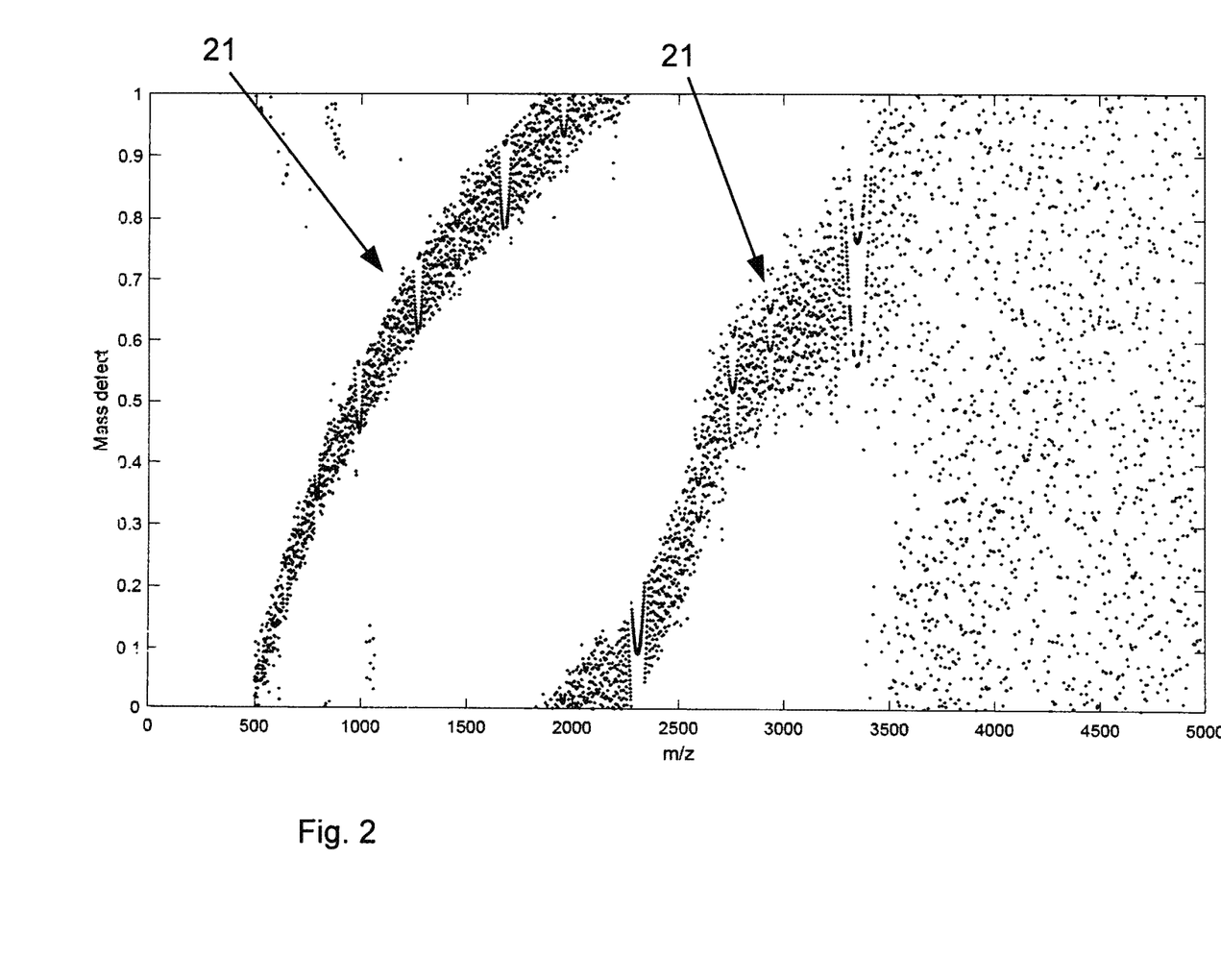
FIG. 2 a conventional mass defect diagram of an average spectrum with recognizable peptide band.

To visualize the mass defects observed in a spectrum, the m/z values of the peaks found in a spectrum are plotted in a diagram, whose horizontal axis corresponds to the mass m (or m/z value), while their decimal places m-floor(m) are plotted on the vertical axis, see FIG. 2. Such diagrams are used to visualize different compositions of complex molecular mixtures. A different version is the so-called Kendrick mass defect diagrams, which are used to characterize chemical compounds of a specific group, see Wikipedia: Kendrick mass. https://en.wikipedia.org/wiki/Kendrick_mass. In the context of investigating peptides, mass defect diagrams can be used to differentiate between peptides and so-called glycopeptides, cf. US 2016/0003842 A1 and Froehlich J et al.: A Classifier Based on Accurate Mass Measurements to Aid Large Scale, Unbiased Glycoproteomics. Mol. Cell. Proteomics 2013, 12, 1017-1025.

Moreover, peptides can specifically be chemically modified in such a way that they exhibit a mass defect which differs significantly from the peptide mass model (also known as an averagine model) and can be distinguished from unmodified peptides with the aid of this deviation, cf. Chen X, Savickas P, Vestal M. Methods and systems for mass defect filtering of mass spectrometry data. U.S. Pat. No. 7,634,364, filed 2006 Jun. 23, granted 2009 Dec. 15; Yao X, Diego P, Ramos A A, Shi Y. Averagine-scaling analysis and fragment ion mass defect labeling in peptide mass spectrometry. Anal. Chem. 2008 Oct. 1; 80(19):7383-91. doi: 10.1021/ac801096e; Sleno L. The use of mass defect in modern mass spectrometry. J. Mass. Spectrom. 2012, 47: 226-236. doi:10.1002/jms.2953

With this method of mass defect filtering, the mass defect determined for a spectral peak is used to chemically characterize the corresponding molecule in more detail. A precondition for this method is thus that the accuracy of the mass determination is sufficiently high.

A representation which differs from the usual mass scale is occasionally used to graphically visualize the mass defect filtering. In this representation the deviation from the nearest mass corresponding to the averagine model in each case is plotted in the vertical direction instead of the mass defect, cf. Yao X, Diego P, Ramos A A, Shi Y. Averagine-scaling analysis and fragment ion mass defect labeling in peptide mass spectrometry, Anal. Chem. 2008 Oct. 1; 80(19):7383-91. doi: 10.1021/ac801096e.

In the particular context, these diagrams serve merely to illustrate the method with the aid of exemplary, synthetically computed peptide masses. No application of this form of representation to actually measured data is known.

A diagram known as a peptide mass defect diagram (PMD) can be created from an average spectrum formed over several spectra of a MALDI measurement. To this end, a list of all local maxima and their respective m/z values is determined, and for each m/z value the deviation from the respective nearest mass corresponding to the theoretical peptide mass model is determined. Assuming that the measured signals are attributable to peptides, for every m/z value m the nominal mass $m_N$ is now determined for which the modulus of the deviation between m and the mass expected according to the theoretical peptide mass model (averagine model, see above) $m_P(m_N)$ is minimized (see below). The minimum deviation $\delta_P(m)$, which can assume values from −0.5 to 0.5, is known as the peptide model distance. The peptide model distance corresponds to the above-described discrepancy between measured and expected mass defect.

The positions of all local maxima are now entered into a diagram whose horizontal axis corresponds again to the mass or the m/z value, and on whose vertical axis the deviation from the peptide mass model determined above is plotted.

Compared to the familiar mass defect diagram, the PMD is therefore generated by means of a transformation which reproduces the positions of the theoretically expected peptide mass defects onto the reference line 22, which is a horizontal zero line. Moreover, the PMD differs from the known representations by virtue of the fact that no prior specific signal analysis is carried out, in particular no identification of significant peptide peaks (peak picking). Rather, the PMD essentially reflects statistical characteristics of the spectral background signal (cf. FIG. 1), the only assumption being that the signal originates largely from peptide molecules. The vertical axis ranges from −0.5 to 0.5 and shows the signed discrepancy between the mass defect expected for a peptide and that which is actually measured.

In addition to the reference line 22, a reference interval can be drawn in with lines 23, 24, which represents the expected variance of the peptide mass defects about their average, taking into account the given discretization of the mass axis for a measurement.

Figure 3:
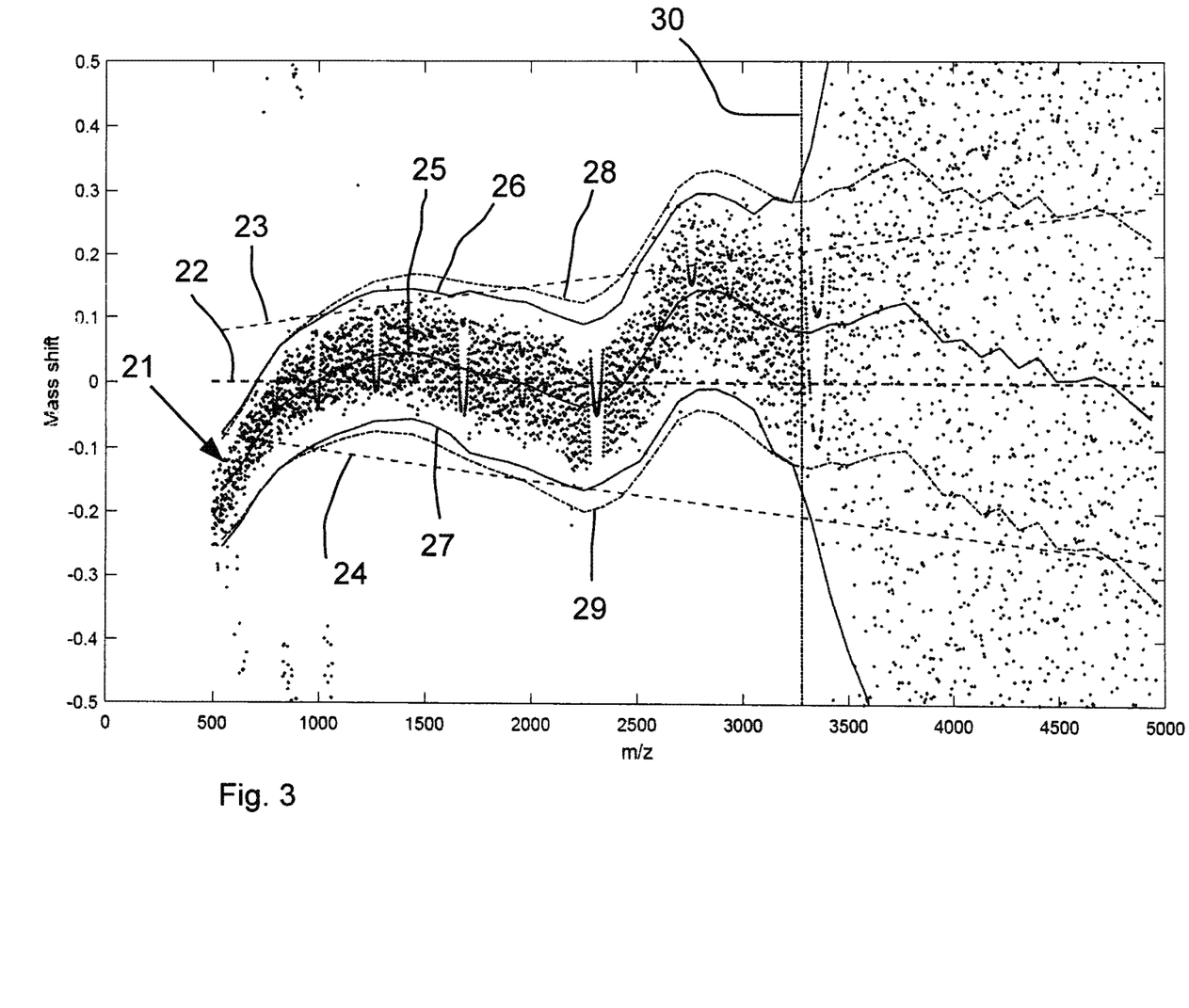
FIG. 3 a peptide mass defect diagram (PMD) of the average spectrum from FIG. 2, i.e. showing a mass shift as a function of the mass (m/z), with horizontal reference line for an expected mass defect and reference interval (broken lines), mass defect discrepancy and its variance (solid line) and expected variance (dash-point-dash lines) and upper limit of the mass range with recognizable peptide signal (dotted line)
Figure 4:
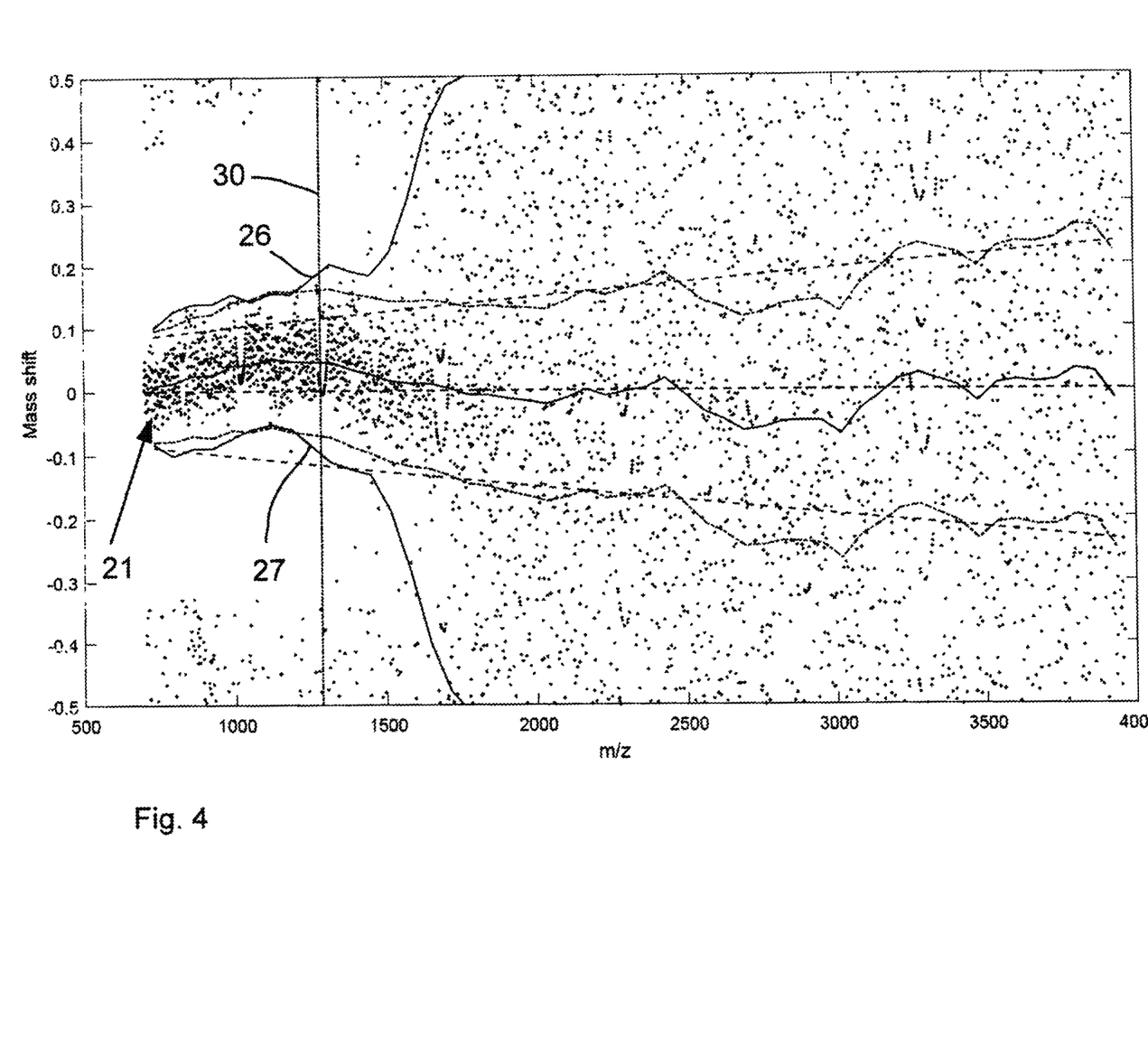
FIG. 4 a PMD of an average spectrum with greatly reduced signal-to-noise ratio, recognizable in the reduced peptide signal range, which extends only to approx. 1300 Da.
Figure 5:
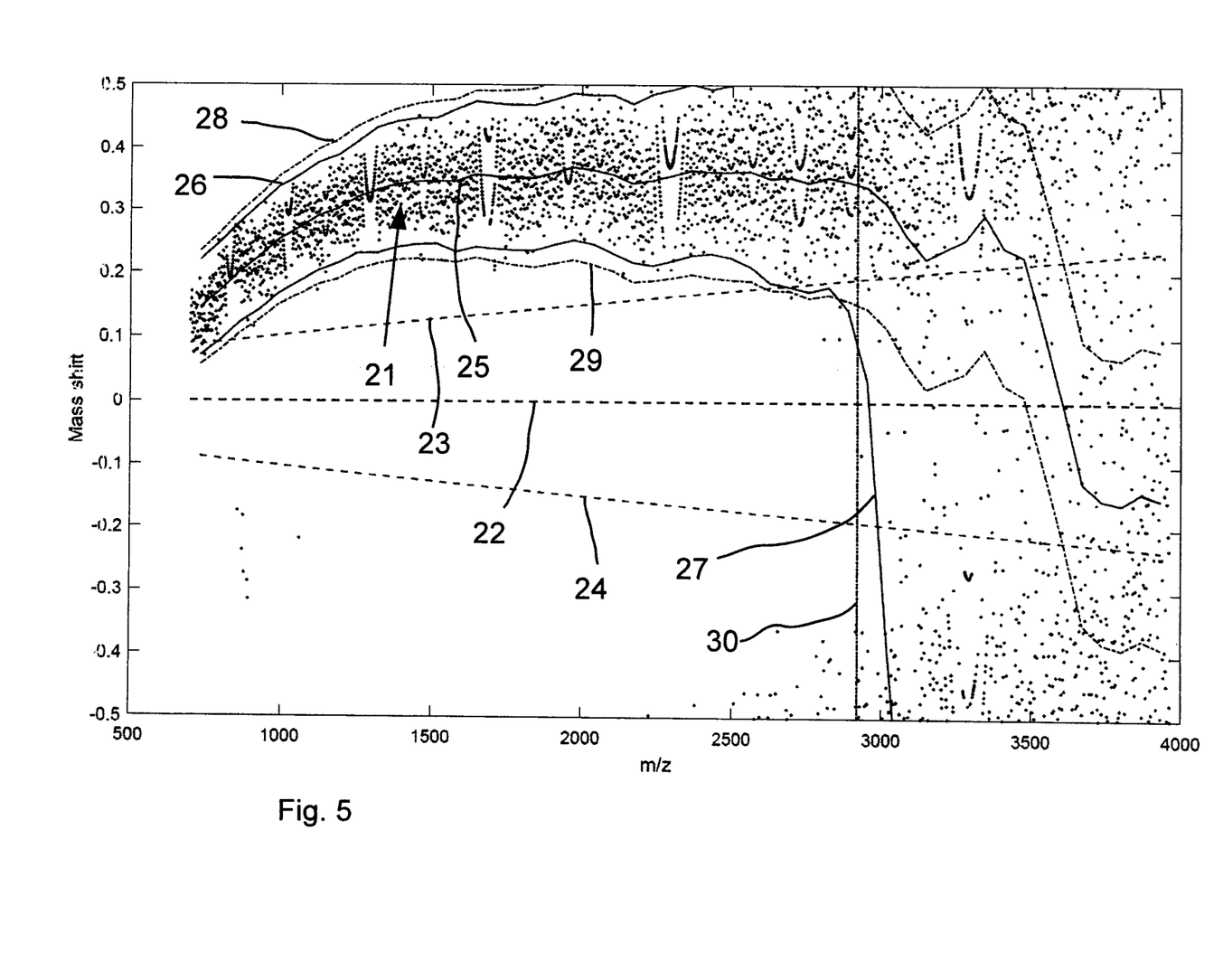
FIG. 5 a PMD of a spectrum with significant mass shift by approx. 0.15 to 0.35 Da.
Figure 6:
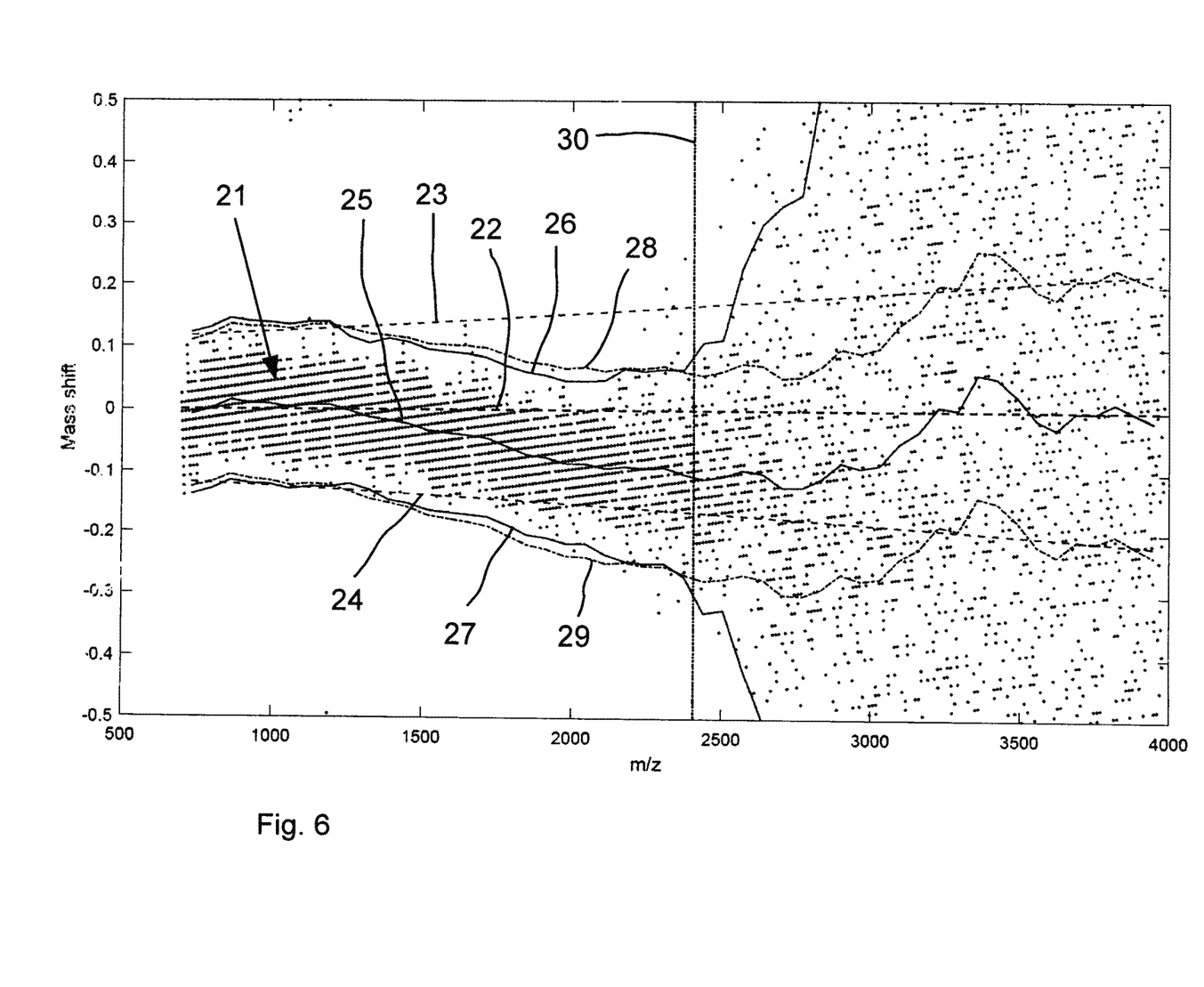
FIG. 6 a PMD with clearly recognizable line structure due to the equidistant sampling of the mass axis.
Figure 7:
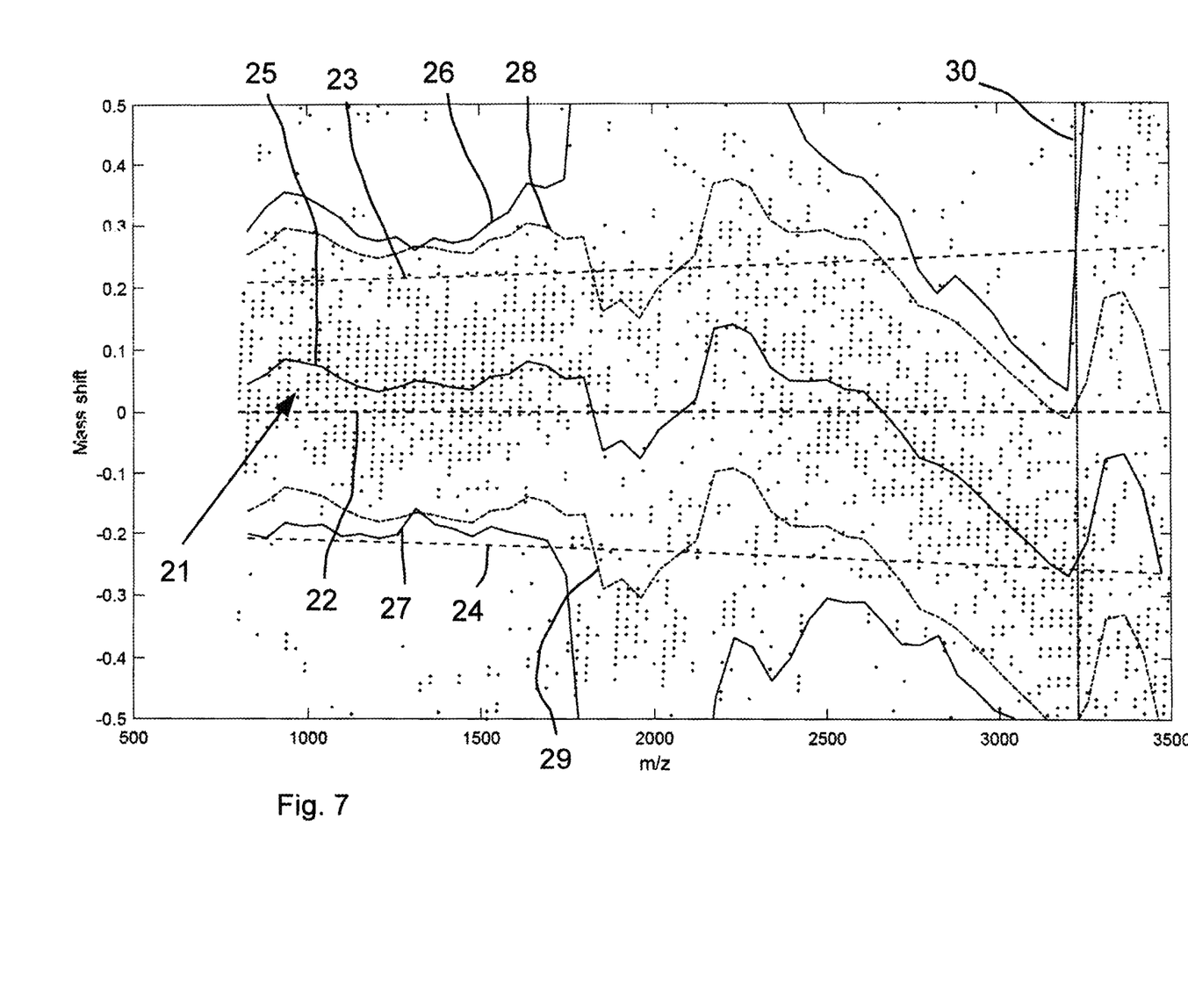
FIG. 7: a PMD of an average spectrum with very coarsely sampled mass axis; the coarse sampling makes it almost impossible to recognize the structure of the peptide band.
Figure 8:
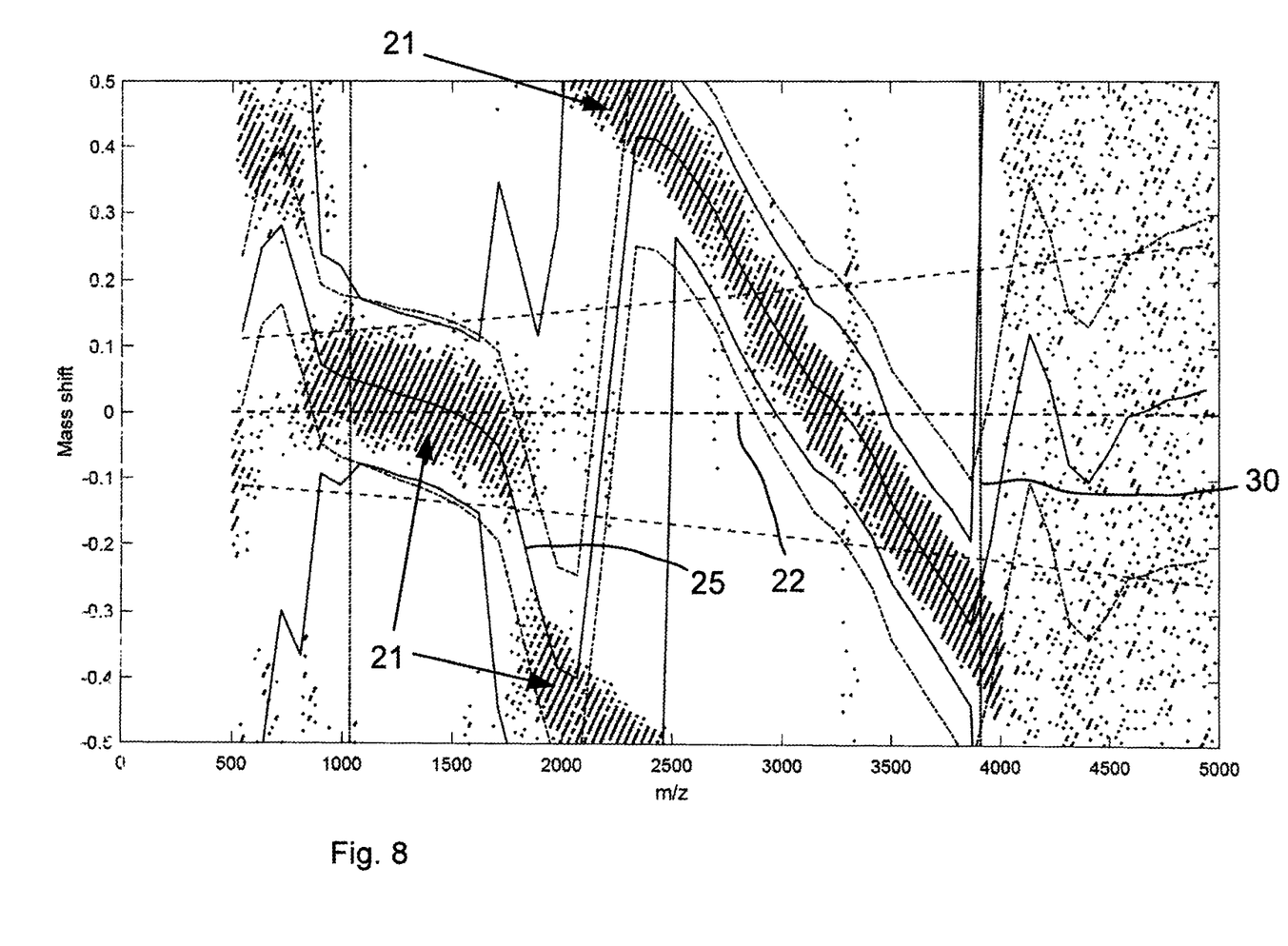
FIG. 8 a PMD of an average spectrum with defectively performed calibration, recognizable by the break in the peptide band as from approx. m/z=1700.

The following quality characteristics of a spectrum can easily be read off from a PMD:
1. Mass range with peptide signals: A clearly recognizable band ("peptide band 21") close to the reference line 22 points to the presence of peptide signals in the mass range in question. Where the band structure is lost in an unstructured point cloud (typically recognizable at the top end of the mass axis, to the right of an upper limit 30), the peptide signal is lost in the noise (FIGS. 3, 4).
2. Mass shift: If the peptide band 21 deviates noticeably from the reference line 22, this points to a discrepancy between the true and the measured molecular masses. The magnitude of the discrepancy corresponds to the vertical offset between reference line 22 and the center line 25 of the peptide band 21. The reference interval here gives the range in which a shift can be explained by the particular discretization of the mass axis (FIGS. 3, 5).
3. Equidistant or too coarsely sampled mass axis: a MALDI-TOF mass spectrometer does not typically discretize the mass axis with equidistant intervals, but with increasing bin width toward high masses. When spectral data are subjected to post-processing, the data are frequently re-sampled onto an equidistant mass axis with lower resolution, causing a loss in accuracy. An equidistant mass axis can be clearly recognized in the PMD by virtue of the fact that the points plotted have a linear structure (FIG. 6). If the resolution of the data is too low after the resampling, the structure of the peptide band 21 (FIGS. 6, 7) is lost.
4. defective calibration of the mass axis: Errors which lead to a discontinuous distortion of the mass axis can occur during the calibration of the mass axis. Such distortions occur in the PMD as a break or offset in the peptide band 21 (FIG. 8).

Compared to visualization with the aid of conventional mass defect diagrams, the above-stated quality characteristics of a spectrum can be recognized much more clearly in a PMD. In particular, even smaller mass shifts, or those restricted to subsections of the mass axis, can be detected more easily as deviations from the horizontal reference line 22.

A PMD can also be formed for an individual spectrum or for the maximum spectrum over several individual spectra (so-called skyline spectrum), rather than for an average spectrum. This representation does not provide as much information, however.

In addition to the pure visualization, the information shown in a PMD can also be evaluated quantitatively as follows (see also mathematical formulation further below):
1. Determination of the discrepancy between measured and expected peptide mass defect as a function of mass. To this end, the median of the mass defects over subintervals of the mass axis is formed and compared with the expected value.
2. Determination of the variance of the mass defects about their average. To this end, the interquartile range of the mass defects is determined over subintervals and converted into a specified multiple of the standard deviation of an assumed normal distribution.
3. Determination of the mass range with recognizable peptide signal. To this end, the variance of the mass defects determined from the data (range between lines 26, 27) is compared with the width of the reference interval (range between lines 23, 24) and the range is determined in which the deviation remains within a selected tolerance.

This quantitative information can be displayed in the PMD and also presented numerically or processed further to evaluate the quality of the measurement.

$$S=(s_j, m_j)_{j=1...n}, \text{ mit } n \in \mathbb{N}, 0 < m_1 < ... < m_n$$

describes an (individual, average or skyline) spectrum which consists of the n intensities $s_1 \ldots s_n$ for the m/z values $m_1 \ldots m_n$.

$$\text{floor}(x) \text{ for } x > 0$$

designates the integer part of a positive number x, where $$\varphi(x) = x - \text{floor}(x) \text{ for } x > 0$$

designates the part of a positive number x after the decimal point.

The PMD of the local maxima of S consists of the graphical representation of the points $$\left\{(m_0 \delta_P(m_i)) : s_i > \max_{0 < |j-i| \le u} s_j\right\}$$

where $u \in \mathbb{N}$ designates the radius of the local environment, via which the local maxima are formed, and the function $$\delta_P(m) = \varphi\left(\frac{m}{1+r_P} + 0.5\right) - 0.5$$

describes the signed discrepancy between the mass defect expected for a peptide and the one actually measured. The above representation of the discrepancy $\delta_P(m)$ is derived as follows:

The theoretically expected mass defect of a peptide with nominal mass $m_N$ is $$m_P - m_N = (1+r_P)m_N - m_N = r_P m_N.$$

For an actually measured mass m of a peptide, its nominal mass is assumed to be the integer mass $m_N$ for which the absolute difference $$|m - (1+r_P)m_N|$$

is minimized. This leads to $$m_N = \text{floor}\left(\frac{m}{1+r_P} + 0.5\right).$$

The discrepancy $\delta_P(m)$ results from the difference between measured and expected mass defect $$\delta_P(m) = \frac{(m - m_N) - (m_P - m_N)}{1 + r_P} =$$

$$\frac{m - (1+r_P)m_N}{1+r_P} = \frac{m}{1+r_P} - \text{floor}\left(\frac{m}{1+r_P} + 0.5\right) = \varphi\left(\frac{m}{1+r_P} + 0.5\right) - 0.5$$

Weighting the difference in the mass defects with $1/(1+r_P)$ serves to normalize $\delta_P(m)$ to the range of values $[-0.5 \ldots 0.5]$.

The reference line 22 of the theoretically expected average mass defects of peptides is described by the zero line $\delta_P=0$. To determine the reference interval (lines 23, 24), the expected variance v(m) of the positions of the local maxima is considered as a function of the mass, which can be estimated by the sum of the variance of the true peptide masses $\sigma^2{}_P$ and the variance originating from the discretization of the mass axis, $$v(m) = \sigma_P^2(m) + \frac{\Delta m(m)^2}{12}.$$

Here $\Delta m(m)$ designates the width of the m/z bins at mass position m. The reference interval is formed by the limiting lines 23, 24 or $$d_P^{1,2}(m) = \pm \mu \sqrt{v(m)},$$

where the scaling factor $\mu>0$ gives the width of the interval as a multiple of a standard deviation (typically $\mu=2$).

For the spectrum S, a partitioning I of the mass axis shall be given in pairs of disjoint intervals $I_k$:

$$I=(I_k)_{k=1\ldots K} \text{ where } K\in \mathbb{N}, \cup_k I_k=[m_1, m_n].$$

For a PMD, in which the points $$(m_i, \delta_P(m_i))_{i\in L} \text{ mit } L = \left\{ i \in \{1 \ldots n\} : s_i > \max_{0<|j-i|\leq u} s_j \right\}$$

are shown, the discrepancy $$E_k = \text{median}\{\delta_P(m_i) : i \in L \cap I_k\}$$

is formed to determine the mass discrepancy E(m) for the subintervals $I_k$. The $E_k$ are shown as points above the respective midpoints of the corresponding subintervals $I_k$, and a suitable interpolation is carried out in between (e.g. linear). The variance e(m) of the mass defects is similarly formed from the interquartile ranges (IQR), $$e_k = \mu \frac{IQR\{\delta_P(m_i): i \in L \cap I_k\}}{2\sqrt{2}\,\text{erf}^{-1}(0.5)},$$

where the scaling factor $\mu>0$ again gives the width of the interval as a multiple of a standard deviation, typically $\mu=2$, and erf designates the Gaussian error function. The mass range with recognizable peptide signal is determined to be that part of the mass axis for which the ratio of observed (lines 26, 27) and expected variance (lines 28, 29) remains below a specified tolerance threshold t:

$$M_P = \left\{ m \in [m_1, m_n] : \frac{e(m)}{\mu\sqrt{v(m)}} \leq t \right\}.$$

A typical tolerance value is t=1.2. The positions of the outer edges of $M_P$ can be drawn in the PMD as vertical lines.

The above-described representation of a spectrum in a PMD can be applied, in principle, for both average spectra and individual spectra. It requires the identification of local maxima in the relevant spectrum, however, and thus a sufficiently high signal-to-noise ratio, which typically does not exist for individual spectra.

This disadvantage can be circumvented by representing the spectra in a peptide mass defect histogram (PMH). This is created by presenting all spectral intensities for all m/z bins of a spectrum in a 2D histogram, in which the horizontal axis again corresponds to the mass axis, and the vertical axis represents the peptide model distance to the relevant mass (see below). Both axes are uniformly subdivided into preselected numbers of subintervals (typically 20-50, can be different for each axis), thus partitioning the diagram area into rectangular tiles.

The spectrum under analysis is now interpolated to an m/z resolution which corresponds to the selected subdivision of the mass defect axis. All those intensity values of the interpolated spectrum whose masses and mass defects fall within the relevant subintervals of the horizontal or vertical axis are then summed for each tile.

Figure 9:
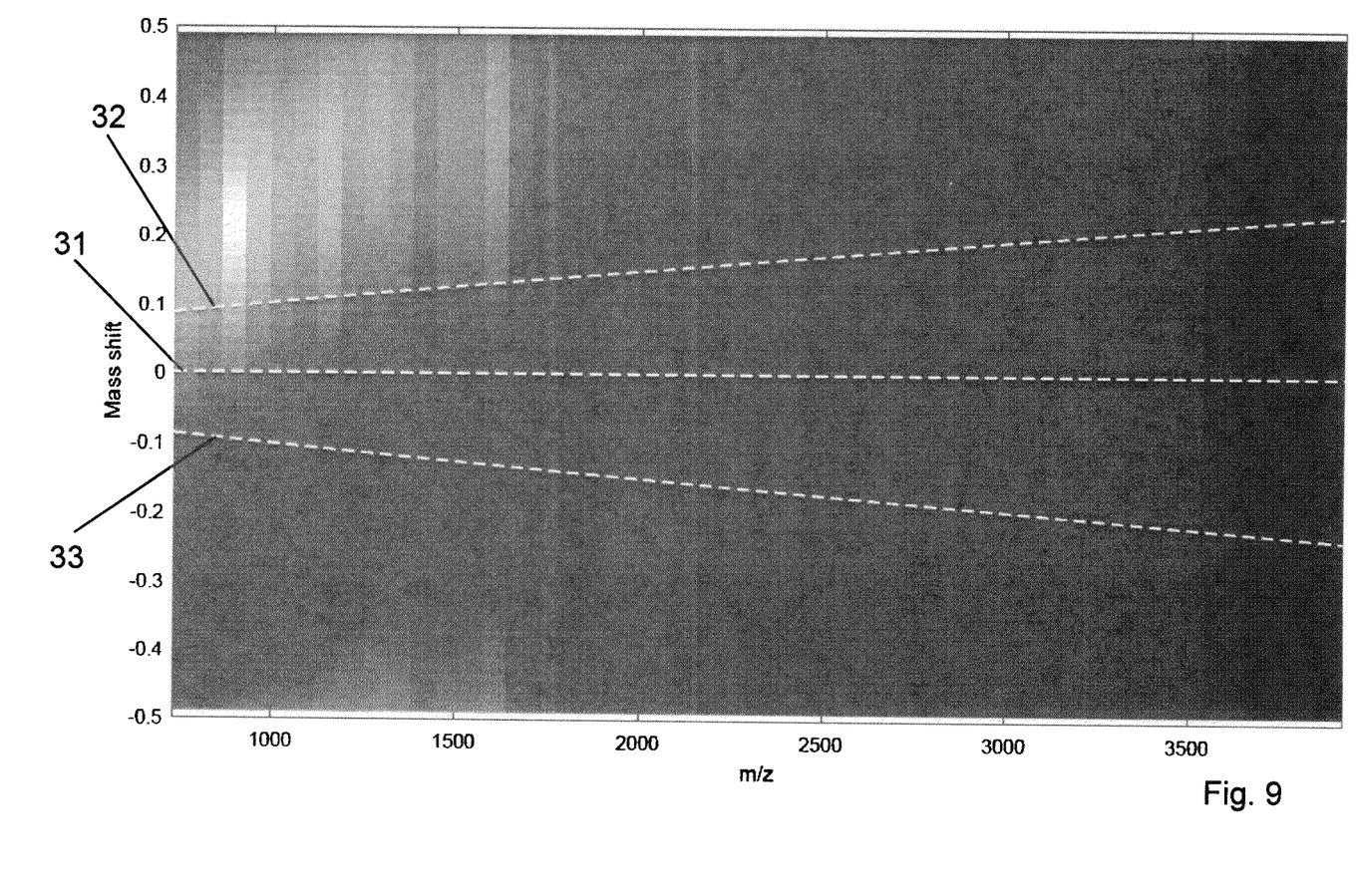
FIG. 9 a peptide mass defect histogram (PMH) of an average spectrum with mass shift comparable to the one shown in FIG. 5.

For the graphical illustration, all the tiles can finally be visualized using a suitably selected gray scale or color scale corresponding to the summed intensities. As in the PMD, the reference line 31 and the reference intervals 32, 33 are additionally drawn in (FIG. 9). The PMH can be interpreted in the same way as the PMD.

In analogy with the quantitative evaluation of a PMD, characteristic quantities of a spectrum can also be calculated from a PMH—and thus also for individual spectra, too. To this end, an evaluation of the vertically arranged summed intensity values is carried out for each subinterval of the horizontal mass axis to determine cluster points and variance values from this.

It must be noted here that the top and bottom edge lines of a PMH, i.e. the points associated with the extreme distance values +0.5 and −0.5, can be considered to be identical. Circular statistics are therefore suitable to describe the distribution of the summed intensity values in the vertical direction. The first circular moment Z in particular can be used as the (complex-valued) statistics (mathematical formulation see below). The circular moments Z for all the subintervals of the mass axis taken together are called the mass shift profile of the spectrum considered. The complex argument of Z corresponds (apart from a factor $2\pi(1+r_P)$) to the discrepancy between measured and expected masses. The value of Z provides a reciprocal measure for the variance of the measured peptide model distances: The value Z=0 corresponds to a maximum variance of all the measurements over the interval [−0.5 . . . 0.5], while in the extreme case of a minimum variance where all distance values are identical, Z assumes a value with modulus 1.

For the actual calculation of the mass shift profile Z, the two steps to form the 2D histogram and the computation of the circular moments can be combined and expressed as Fourier integrals of the spectrum over the subintervals of the mass axis (see below). These integrals can be numerically approximated with the aid of suitable integration rules (for example the trapezoidal rule or Simpson's rule). It is also possible here to forgo a finer discretization and interpolation of the spectrum and to calculate directly with the discrete spectral intensities in the resolution originally available.

The mass shift profile provides an estimate of the measurement errors of the measured masses occurring in a spectrum with respect to the true masses. In practice it is often desirable to correct these shifts and thus achieve a higher accuracy for the measured masses of a spectrum.

On the other hand, the mass shift profile is obtained by comparing the measured data with the relatively simple, linear averagine model (see above). The estimation of the mass errors through the mass shift profile cannot therefore be more accurate than the accuracy of the model itself, which is not sufficiently high for many applications, at least in the lower mass range up to approx. 1,000 Da. A correction of the measured masses by the estimated measurement error can therefore lead to parts of the measurement becoming less accurate.

For many applications, however, it is not absolute mass accuracy which is decisive, but rather the best possible comparability between individual spectra from one and the same or from several measurements. The absolute measurement error of the measured masses of a spectrum is less relevant in these cases than the differences of the measurement errors within an ensemble of spectra.

Figure 10:
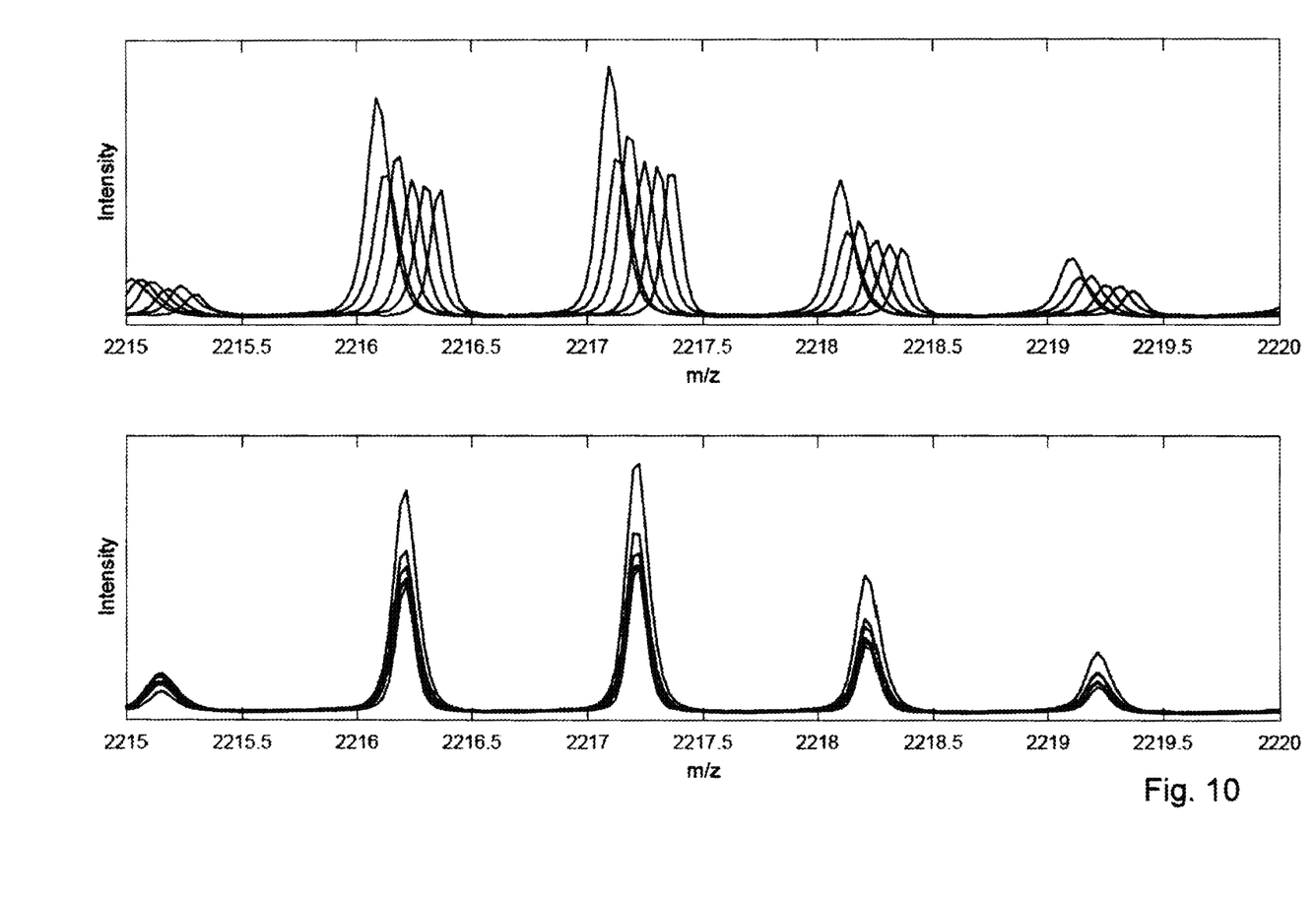
FIG. 10 average spectra before (top) and after (bottom) mass shift normalization.

The method of mass shift normalization consists in initially determining the respective mass shift profile for each spectrum in an ensemble (see above), forming a common, average reference profile from all the individual mass shift profiles, and finally modifying each spectrum in such a way that the mass shift profile of the modified spectrum corresponds to the reference profile. The relative deviation between the signal peaks of the individual spectra belonging to one and the same peptide is reduced, and the comparability of the spectra is enhanced (FIG. 10, bottom) by this approximation.

The reference profile is determined by forming the arithmetic mean element by element (see below). To normalize a single spectrum to the reference profile, relative shift values are determined for the individual subintervals for which the mass shift profiles were calculated, and these values are interpolated over the whole mass axis. The measured mass values of the spectrum are then corrected by these interpolated shift values.

By applying these shifts, each individual spectrum is given its own mass axis. For a joint evaluation of an ensemble of spectra, it is usually desirable for all spectra to be defined on a common mass axis. This can be achieved by forming a common mass axis (for example by averaging over all the individual mass axes or by selecting an arbitrary mass axis as the reference mass axis) and subsequently interpolating each normalized spectrum to the common mass axis.

Peptide mass defect histogram:

$$S=(s_j, m_j)_{j=1 \ldots n}, \text{ mit } n \in \mathbb{N}, 0 < m_1 < \ldots < m_n$$

designates, as above, an (individual, average or skyline) spectrum consisting of the n intensities $s_1 \ldots s_n$ for the m/z values $m_1 \ldots m_n$.

As above, for a spectrum S, there shall be a partitioning I of the mass axis as well as a further partitioning J of the interval [−0.5 . . . 0.5], $$I=(I_k)_{k=1, \ldots, K} \text{ where } K \in \mathbb{N}, \cup_k I_k = [m_1, m_n],$$

$$J=(J_l)_{l=1, \ldots, L} \text{ where } L \in \mathbb{N}, \cup_l J_l = [-\frac{1}{2}, \frac{1}{2}].$$

For the partitionings I and J, $$\Gamma_{k,l} = \{m \in I_k : \delta_P(m) \in J_l\}$$

provides a finer partitioning of the mass axis, where the subintervals $\Gamma_{k,l}$ are assigned to the individual tiles of the 2D histogram. Furthermore, an interpolating line of the spectrum S shall be given by a continuous function $\tilde{S}(m)$, $$\tilde{S}:[m_1, m_n] \to \mathbb{R}, \text{ mit } \tilde{S}(m_j)=s_j, j=1 \ldots n.$$

The matrix $H(S)=(h_{k,l})$ shall be defined by $$h_{k,l} = \frac{1+r_P}{\int_{I_k} \tilde{S}(t) dt} \int_{\Gamma_{k,l}} \tilde{S}(t) dt \text{ für } k = 1 \ldots K, l = 1 \ldots L$$

For numerical calculation of $h_{k,l}$, one can select $\tilde{S}$ as a linear interpolant of S, for example. The integrals can then be evaluated exactly. To form the PMH, the matrix H(S) is depicted as a gray scale or false color image.

Mass Shift Profile:

With the designations and definitions of the previous section, the first circular moment of the columns of H is given by the complex quantities $$Z_k = \sum_{l=1}^{L} h_{k,l} e^{2\pi i \tilde{\delta}_l},$$

where $\tilde{\delta}_l$ designates the average values of the intervals $J_l$. In the limiting case of an infinitesimally fine partitioning J (i.e. L→∞) the $Z_k$ can be represented by $$Z_k = \frac{1}{\int_{I_k} \tilde{S}(t) dt} \int_{I_k} \tilde{S}(t) e^{i\omega t} dt, \text{ mit } \omega = \frac{2\pi}{1+r_P}$$

For the specific numerical calculation of these integrals, a suitable integration formula (e.g. trapezoid formula or Simpson's rule), and as reference points of $\tilde{S}$ especially the discrete measurement points $(m_j)_{j=1 \ldots n}$ can be selected. Because of $\tilde{S}(m_j)=s_j$, it is then not necessary to explicitly interpolate the spectrum S.

Mass Shift Normalization:

There shall be an ensemble of N spectra $S^i (i=1 \ldots N)$, which have a common mass axis $(m_j)_{j=1 \ldots n}$. Furthermore, there shall be a partitioning I of the mass axis into K subintervals, as above. The mass shift profiles computed for these partitionings for the individual spectra $S^i$ shall be designated by $Z^i$:

$$Z^i = (Z_k^i)_{k=1 \ldots K} \text{ für } i=1 \ldots N$$

For the mass shift profiles $Z^i$, the reference profile $\overline{Z}$ is calculated by forming the arithmetic mean, element by element:

$$\overline{Z} = (\overline{Z}_k)_{k=1 \ldots K} \text{ mit } \overline{Z}_k = \frac{1}{N} \sum_{i=1}^{N} Z_k^i.$$

Now $S=(s_j, m_j)_{j=1 \ldots n}$ shall be an arbitrary spectrum defined over the same mass axis with mass shift profile $Z=(Z_k)_{k=1 \ldots K}$. For each subinterval of the partitioning I, a relative displacement $$\Delta_k = \frac{1}{2\pi}(\arg(Z_k) - \arg(\overline{Z}_k))$$

is now determined, where $\arg(z) \in (-\pi, \pi]$ designates the complex argument function. The individual shifts $\Delta_k$ are assigned to the midpoints of the subintervals $I_k$ and interpolated over the complete mass axis (typically by means of linear interpolation). A shift vector $\Delta^\wedge = (\Delta_j)_{j=1 \ldots n}$ is thus obtained. The normalized spectrum $S^\wedge$ is obtained by applying the shift values to the m/z values of the spectrum S, $$S^\wedge = (s_j, m_j)_{j=1 \ldots n}, \text{ mit } m_j^\wedge = m_j + \Delta_j.$$

KEY

20 Base line
21 Peptide band

22 Reference line
23 Line for reference interval
24 Line for reference interval
25 Center line as mass defect discrepancy
26 Line for mass defect variance
27 Line for mass defect variance
28 Line for expected variance
29 Line for expected variance
30 Upper limit
31 Reference line
32 Line for reference interval
33 Line for reference interval

The invention claimed is:

1. Method to evaluate mass spectrometry data for the analysis of peptides from biological samples, particularly MALDI-TOF mass spectrometry data, comprising the following steps:
   a) provide expected mass defects;
   b) determine measured mass defects, i.e. the mass defects resulting from the mass spectrometry data;
   c) compare the measured mass defects with the expected mass defects,
   wherein
   a peptide mass defect diagram (PMD) is created from an average spectrum formed over a plurality of spectra of a MALDI measurement,
   including
   determining a list of local maxima and their respective m/z values, wherein for each m/z value a deviation from a respective nearest mass corresponding to a theoretical peptide mass model is determined,
   determining for every m/z value m a nominal mass $m_N$ for which a modulus of the deviation between m and the mass expected according to the theoretical peptide mass model $m_P(m_N)$ is minimized, wherein a minimum deviation can assume values from −0.5 to 0.5, and
   entering positions of local maxima into the diagram whose horizontal axis corresponds to the mass or the m/z value, and on whose vertical axis the deviation from the theoretical peptide mass model determined above is plotted.

2. The method according to claim 1, wherein the expected mass defects are calculated from $$m_N r_P,$$

where $m_N$ designates the nominal mass of a peptide and $r_p$ is a scalar between $10^{-3}$ and $10^{-4}$.

3. The method according to claim 1, wherein the mass defect for a measured mass m is calculated from $$m - \text{floor}\left(\frac{m}{1+r_p} + 0.5\right),$$

where the function floor(x) for an arbitrary x>0 designates the integer part of x.

4. The method according to claim 1, wherein the discrepancy $\delta_P$ between the measured and the expected mass defect is calculated directly from the measured mass m as $$\delta_P(m) = \varphi\left(\frac{m}{1+r_p} + 0.5\right) - 0.5$$

where the function $\varphi(x)=x-\text{floor}(x)$ designates the decimal places of x for any x>0.

5. The method according to claim 1, wherein the median of the measured mass defects is formed and compared with the expected mass defect in order to compare the measured mass defects with the expected mass defects over subintervals of a mass axis.

6. The method according to claim 1, wherein the measured values are corrected when the data are to be used further, i.e. depending on the deviation of the measured mass defects from the expected mass defects.

7. The method according to claim 1, wherein the measured mass defects are calculated for local maxima of the spectral intensities.

8. Mass spectrometric method for the analysis of peptides from biological samples, particularly by means of a MALDI TOF mass spectrometer, comprising the following steps:
   a) carry out one or more mass spectrometric analyses on the biological sample and provide data which result from the mass spectrometric analyses;
   b) carry out the method according to claim 1.

9. MALDI-TOF mass spectrometer with a control unit for the analysis of peptides from biological samples using a method according to claim 1.

10. The method according to claim 1, further including using at least one of calculatory and visual means in order to assess a quality of the data on the basis of the comparison in step c).

* * * * *